(12) United States Patent
Jia et al.

(10) Patent No.: US 7,892,811 B2
(45) Date of Patent: Feb. 22, 2011

(54) CONTROLLED LYSIS OF BACTERIA

(75) Inventors: Xiyu Jia, Newport Beach, CA (US); Jan Kostal, Saint Paul, MN (US); Jonathan Anthony Claypool, Seattle, WA (US)

(73) Assignee: Zymo Research Corporation, Irvine, CA (US)

( * ) Notice: Subject to any disclaimer, the term of this patent is extended or adjusted under 35 U.S.C. 154(b) by 748 days.

(21) Appl. No.: 11/205,867

(22) Filed: Aug. 16, 2005

(65) Prior Publication Data

US 2006/0040393 A1 Feb. 23, 2006

Related U.S. Application Data

(60) Provisional application No. 60/602,520, filed on Aug. 17, 2004.

(51) Int. Cl.
*C12N 1/21* (2006.01)
(52) U.S. Cl. .............. 435/252.33; 435/235.1; 435/259; 435/69.1; 435/173.7
(58) Field of Classification Search .............. None
See application file for complete search history.

(56) References Cited

U.S. PATENT DOCUMENTS

| | | | |
|---|---|---|---|
| 4,637,980 A * | 1/1987 | Auerbach et al. ......... | 435/69.3 |
| 4,952,496 A | 8/1990 | Studier | |
| 5,550,035 A | 8/1996 | Moss | |
| 5,693,489 A | 12/1997 | Studier | |
| 5,824,528 A | 10/1998 | Studier | |
| 5,830,694 A | 11/1998 | Studier | |
| 5,869,320 A | 2/1999 | Studier | |
| 6,896,882 B2 * | 5/2005 | Ramachandran et al. ... | 424/93.2 |
| 2006/0240522 A1 * | 10/2006 | Leung et al. ............ | 435/69.1 |

OTHER PUBLICATIONS

Studier et al., 1986, J. Mol. Biol. 189: 113-130. Use of Bacteriophage T7 RNA PLoymerase to Direct Delective High-level Expression of cloned Genes.
Studier et al., 1990, Methods in Enzymol. 185: 60-89. Use of T7 RNA Polymerase to Direct Expression of Cloned Genes.
Chang C.Y. et al., J. Bacteriol. Jun. 1995; 177(11): 3283-3294. S Gene Expression and the Timing of Lysis by Bacteriophage LAMBDA.
Young et al., 1992 Microbiolgical Reviews, Sep. 430-481. Bacteriophage Lysis: Mechanism and Regulation.
Datsenko and Wanner 2000, P.N.A.S., Jun. 6, vol. 97, 6640-6645. One-Step inactivation of chromosomal genes in *Escherichia coli* K-12 using PCR products.
Cherepanov and Wackernagel 1995, Gene 158: 9-14. Gene disruption in *Escherichia coli*: TcR and KmR cassettes with the option of Flp-catalyzed excision of the antibiotic-resist.
Smith, B.R. and Schleif, R. 1978, Journal Of Biological Chemistry, vol. 253, No. 9 pp. 6931-6933. : Nucleotide Sequence of the L-Arabinose Regulatory Region of *E. coli*.
Koonin and Rudd 1994, Trends in Biochem. Sci. 19:106-107. A conserved domain in putative bacterial and bacteriophage transglycosylases.
Novagen, Lambda DE3 Lysogenization Kit, Product Information: TB031.

* cited by examiner

*Primary Examiner*—James S Ketter
(74) *Attorney, Agent, or Firm*—Jonathan A Claypool

(57) ABSTRACT

The present invention relates to the simple, gentle, and efficient extraction of biological material from *Escherichia coli* (*E. coli*). The use of *E. coli* in research laboratories depends on the ability to prepare lysates to isolate the desired products under investigation. The present invention includes methods and engineered *E. coli* strains that are capable of rapid controlled lysis or herein "autolysis". The XJa strains were made from JM109 and the XJb strains from BL21 by insertion of the λ R or (λ SR) lytic endolysin gene to replace the tightly regulated araB gene. Thus, arabinose becomes a non-metabolizable inducer and the controlled autolysis phenotype is induced by the $P_{BAD}$ promoter by the presence of saturating arabinose. Upon induction of the bacteriophage λR endolysin, the *E. coli* remains intact but is efficiently lysed after one freeze-thaw cycle. The present invention is usable with many different buffer systems and is flexible in this regard. The controlled autolysis phenotype shows increased yields and purity of extracted protein compared to detergent based lysis or traditional sonication lysis methods. The present invention is useful for routine protein expression or nucleic acid extraction and also for high-through-put manipulation involving protein or nucleic acid from *E. coli*.

11 Claims, 10 Drawing Sheets

*E.coli* (WT) ::λWT

Step 1   Chromosomal PCR

Step 2   Mixed Template PCR

Step 3   Chromosomal Recombination Screen for Cm^R

Step 4   FLP Recombinase Screen for Cm^S

A

B

SEQUENCE LISTING

<160> NUMBER OF SEQ ID NOS: 11

<210> SEQ ID NO 1
<211> LENGTH: 64
<212> TYPE: DNA
<213> ORGANISM: Artificial Sequence
<220> FEATURE:
<223> OTHER INFORMATION: lambda amplification
<220> FEATURE:
<221> NAME/KEY: RBS
<222> LOCATION: (23)..(27)
<220> FEATURE:
<221> NAME/KEY: Primer
<222> LOCATION: (23)..(27)

<400> SEQUENCE: 1
ctgtttctcc atacccgaaa aaggaggaaa aaaaatgcca gaaaaacatg acctgttggc    60
cgcc    64

<210> SEQ ID NO 2
<211> LENGTH: 68
<212> TYPE: DNA
<213> ORGANISM: Artificial Sequence
<220> FEATURE:
<223> OTHER INFORMATION: lambda amplification
<220> FEATURE:
<221> NAME/KEY: RBS
<222> LOCATION: (23)..(27)
<220> FEATURE:
<221> NAME/KEY: Primer
<222> LOCATION: (23)..(27)

<400> SEQUENCE: 2
ctgtttctcc atacccgaaa aaggaggaaa aaaaatggta gaaatcaata atcaacgtaa    60
ggcgttcc    68

<210> SEQ ID NO 3
<211> LENGTH: 54
<212> TYPE: DNA
<213> ORGANISM: Artificial Sequence
<220> FEATURE:
<223> OTHER INFORMATION: Site I on pKD3 and 3' end of lambda R
<220> FEATURE:
<221> NAME/KEY: misc_feature
<222> LOCATION: (1)..(54)
<220> FEATURE:
<221> NAME/KEY: Primer
<222> LOCATION: (1)..(54)

<400> SEQUENCE: 3
cgaagcagct ccagcctaca caatcgctcg ctcatacatc aatctctctg accg    54

<210> SEQ ID NO 4
<211> LENGTH: 64
<212> TYPE: DNA
<213> ORGANISM: Artificial Sequence
<220> FEATURE:
<223> OTHER INFORMATION: Mixed Template Primer
<220> FEATURE:
<221> NAME/KEY: RBS
<222> LOCATION: (60)..(64)
<220> FEATURE:
<221> NAME/KEY: Primer
<222> LOCATION: (60)..(64)
<220> FEATURE:
<221> NAME/KEY: Primer
<222> LOCATION: (60)..(64)

```
<400> SEQUENCE: 4
gcggatccta cctgacgctt tttatcgcaa ctctctactg tttctccata cccgaaaaag    60
gagg                                                                 64

<210> SEQ ID NO 5
<211> LENGTH: 72
<212> TYPE: DNA
<213> ORGANISM: Artificial Sequence
<220> FEATURE:
<223> OTHER INFORMATION: Mixed Template Primer
<220> FEATURE:
<221> NAME/KEY: misc_feature
<222> LOCATION: (1)..(72)
<220> FEATURE:
<221> NAME/KEY: Primer
<222> LOCATION: (1)..(72)

<400> SEQUENCE: 5
ttatcaaaaa tcgtcattat cgtgtcctta tagagtcgca acggccatgg tccatatgaa    60
tatcctcctt ag                                                        72

<210> SEQ ID NO 6
<211> LENGTH: 19
<212> TYPE: DNA
<213> ORGANISM: Artificial Sequence
<220> FEATURE:
<223> OTHER INFORMATION: Diagnostic Primer
<220> FEATURE:
<221> NAME/KEY: misc_feature
<222> LOCATION: (1)..(19)
<220> FEATURE:
<221> NAME/KEY: Primer
<222> LOCATION: (1)..(19)

<400> SEQUENCE: 6
gcgggaccaa agccatgac                                                 19

<210> SEQ ID NO 7
<211> LENGTH: 19
<212> TYPE: DNA
<213> ORGANISM: Artificial Sequence
<220> FEATURE:
<223> OTHER INFORMATION: Diagnostic Primer
<220> FEATURE:
<221> NAME/KEY: misc_feature
<222> LOCATION: (1)..(19)
<220> FEATURE:
<221> NAME/KEY: Primer
<222> LOCATION: (1)..(19)

<400> SEQUENCE: 7
ccgttatcag ttccctccg                                                 19

<210> SEQ ID NO 8
<211> LENGTH: 20
<212> TYPE: DNA
<213> ORGANISM: Artificial Sequence
<220> FEATURE:
<223> OTHER INFORMATION: Diagnostoc Primer
<220> FEATURE:
<221> NAME/KEY: misc_feature
<222> LOCATION: (1)..(20)
<220> FEATURE:
<221> NAME/KEY: Primer
<222> LOCATION: (1)..(20)

<400> SEQUENCE: 8
ggtcagttcg agcataaggc                                                20
```

```
<210> SEQ ID NO 9
<211> LENGTH: 20
<212> TYPE: DNA
<213> ORGANISM: Artificial Sequence
<220> FEATURE:
<223> OTHER INFORMATION: Diagnostic Primer
<220> FEATURE:
<221> NAME/KEY: misc_feature
<222> LOCATION: (1)..(20)
<220> FEATURE:
<221> NAME/KEY: Primer
<222> LOCATION: (1)..(20)

<400> SEQUENCE: 9
ggcagcgccg cgttgaactg                                               20

<210> SEQ ID NO 10
<211> LENGTH: 20
<212> TYPE: DNA
<213> ORGANISM: Artificial Sequence
<220> FEATURE:
<223> OTHER INFORMATION: Diagnostic Primer pKD3
<220> FEATURE:
<221> NAME/KEY: Primer
<222> LOCATION: (1)..(20)

<400> SEQUENCE: 10
ttatacgcaa ggcgacaagg                                               20

<210> SEQ ID NO 11
<211> LENGTH: 19
<212> TYPE: DNA
<213> ORGANISM: Artificial Sequence
<220> FEATURE:
<223> OTHER INFORMATION: Diagnostic Primer pKD3
<220> FEATURE:
<221> NAME/KEY: Primer
<222> LOCATION: (1)..(19)

<400> SEQUENCE: 11
gatcttccgt cacaggtag                                                19
```

CONTROLLED LYSIS OF BACTERIA

CROSS REFERENCE TO RELATED APPLICATIONS

This application claims priority to U.S. provisional application 60/602,520 Aug. 17, 2004.

BACKGROUND OF THE INVENTION

1. Field of the Invention

The present invention relates to strains and methods for simple and efficient extraction of biological material from bacteria. The use of *Escherichia coli* (*E. coli*) and other commonly used microorganisms in research laboratories depends on the ability to prepare lysates to isolate the desired products under investigation. The present invention includes engineered *E. coli* strains that are inducible for rapid controlled lysis referred herein to as "autolysis". The XJa strain was made from parental JM109 or BL21 strains by insertion of a chromosomally-encoded lytic gene to replace the tightly regulated araB gene. Thus, arabinose becomes a non-metabolizable inducer that induces the controlled autolysis phenotype. Upon induction of the λ R endolysin the *E. coli* remain physically intact but are efficiently lysed after one freeze-thaw cycle. The present invention is usable with many different buffer systems and is flexible in this regard. The controlled autolysis phenotype shows increased yields and purity of extracted protein compared to traditional lysozyme digestion, detergent based buffers, the harsh sonication, or French press mediated lysis methods. The present invention is useful for routine protein expression, isolation of nucleic acids, or other cellular material. In addition it is useful for high-through-put manipulation involving extraction of such material from *E. coli.*, related bacteria, and other microorganisms known and commonly used in the art 2. Description of the Related Art The need for simple and efficient extraction of material from bacteria such as *E. coli*, and other microorganisms is an ongoing concern for research scientists. Advances in the study of recombinant proteins had led to numerous methods together with variations to address common problems associated with obtaining complete lysis of the samples. Traditional protocols utilize purified preparations of lysozyme to generate spheroplasts and this method is still in common usage. Use of lysozyme has problems in that commercial preparations are often contaminated to some degree with lytic as well as other enzymes that can prematurely lyse the cells, degrade proteins, or nucleic acids. Also the lysozyme is an approximately 15 kDa protein that can mask or interfere with or mask proteins that are being expressed. Modified methods to solve these problems include using reduced concentrations of lysozyme (Marvin and Witholt 1987), osmotic shock, treatment with chloroform (Ames et al. 1984), and use of polymixin B, especially for release of periplasmic proteins (Cerny and Tueber 1971). However, they are inconsistent and do not completely solve the limitation of this method.

The use of a French press to lyse bacterial cultures is useful for large volume samples, but the limited availability of such equipment and high cost are often prohibitive. In addition the use of a French press is time consuming and not well suited for small samples or high throughput sample processing (Goeddel et al 1979, Schumacher et al. 1986). Use of sonication for bacterial lysis is common and ensures thorough lysis, but has troubles of increased sample handling time and heat generation both of which can be problematic, especially for screening purposes. Both the French press and sonication methods mediate extremely severe lysis that further disrupts and releases membrane proteins that can interfere with the purification of target proteins. The method of successive freeze thaw cycles is both time consuming and inefficient. This method often leads to degradation and also suffers from populations of unlysed or incompletely lysed cels. The use of detergent and salt containing buffers to mediate lysis, some of which are commercially available, are somewhat convenient, but suffer in that they introduce of materials that later can be problematic in enzymatic or functional assays (Novagen Corp). In addition they are not effective at extracting large molecular weight proteins.

The bacteriophage T7 lysozyme commercially available and encoded by the plasmid variants pLyseS, or pLyseE can be used to facilitate lysis, since the T7 enzyme can degrade the peptidoglycan cell wall. However, functionally strains carrying these genes are extremely fragile due to basal level expression. Also the system sometimes does not produce significant amounts of recombinant protein (Studier, 1990, Novagen Corp). The T7 lysozyme also inhibits T7 RNA polymerase and so is intended to reduce basal or leaky expression of potentially burdensome proteins until induction of the recombinant protein is desired. In addition the lytic enzymes of other well studied bacteriophages, or organisms could also be used, but have not been developed adequately for efficient lysis of *E. coli* or other bacteria for primary use in recombinant protein production methods to date (Young et al. 1992).

Thus there exists a strong need for improved methods of bacterial lysis to facilitate high-through put screening and also to reduce cost and sample handling time. The first step in obtaining material such as recombinant protein or nucleic acids from bacterial cells is to efficiently break them open, or lyse them. This fundamental process continues to be problematic in part due to the bacterial cell wall. There exists a need of alternative improved methods. The ability to rapidly and gently lyse bacteria would additionally enhance protein purification high-through put analysis and would also result in significant savings of time and money.

SUMMARY

The present invention provides engineered *E. Coli* strains and methods for fast, reliable, efficient, and gentle extraction of biological material for use in a variety of molecular biology experiments. The strains are suitable for routine bacterial lysis for uses in protein purification, protein assays, as well as for rapid nucleic acid isolation procedures. The *E. coli* strains represented by embodiments of the invention also allow significant savings in time, effort, and money. Additionally, bacterial and bacteriophage encoded lytic genes, preferably lytic transglycoslylases, by inducible genomic promoters such the arabinose operon $p_{BAD}$ promoter, are contemplated as embodiments of the present invention. These include, but are not limited to enzymes capable of degrading mureine by cleaving the β-1,4-glycosidic bond between N-acetylmuramic acid and N-acetylglusosamine. Specific genes considered to function similarly to the λ R gene in the present invention include, but are not limited to the putative product from the *E. coli* YfhD gene, the vproduct of the *E. coli* sit gene, the product of the YafG gene, the bacteriophage T7 gp 16 gene, the phage PRD1 gene, the Alteromonas TBTCI resistance gene (tributyltin chloride resistance-conferring protein).

In a preferred embodiment of the present invention the mild expression of a chromosomally encoded bacteriophage λ R endolysin gene (also referred to sometimes as lambda lysozyme) is induced during growth by the addition of arabinose (Chang et al. 1995, Young et al. 1992). The λ R gene encodes a soluble transglycosylase which accumulates intracellular and normally functions with the S inner membrane protein that acts to permeabilize the membrane to allow λ R access to the peptidoglycan cell wall. The expression of a similarly constructed λ SR cassette is an additional embodiment of the invention.

The cells are harvested by centrifugation intact and the peptidoglycan layer of the bacterial cell wall remains protected from digestion by the inner cytoplasmic membrane. However, the cells inner membrane is vulnerable to a brief physical-chemical stress such as that generated by a single freeze-thaw cycle, despite the absence of λ S protein (FIG. 3). In alternative embodiments, both λ R and λ S may both be placed either singly under arabinose control or alternatively under the regulatory control of another of E. coli regulatory promoters to differentially control the lysis of the bacterial cells. Further embodiments of the present invention contemplate placing one or more lytic enzymes from numerous well studied organisms known in the art under inducible regulatory control in the E. coli genome. Such lytic enzymes would be capable of degrading the bacterial cell wall to facilitate controlled lysis, or "autolysis".

The method is rapid and takes only approximately one minute to accomplish (unlike multiple freeze-thaw cycles or sonication, or French press). The method of the present invention can be used with any number of samples without any significant increase in sample processing time or effort. The method is reliable and shows little variation between samples (unlike traditional lysozyme treatments). Embodiments are compatible with a wide range of buffers known and used in the art many of which are commercially available. Additionally, embodiments do not introduce or require potentially interfering components such as detergents commonly found in different lysis buffers, though their addition t low levels enhances lysis to completion.

The E. coli strains of the present invention or strains used for comparison purposes are depicted in Table 4. The parental JM109 strain was utilized for the engineering of XJa strains and BL21 was used for generating XJb strains (Yanish-Perron et al. 1985; Studier and Moffat 1986). The related DE3 lysogenic strains were made via commercially available systems (Novagen Corp).

The λ R endolysin gene was amplified via PCR from a wild type E. coli 533 strain containing a wild-type λ lysogen in the chromosome with primers (Sequence ID-No.'s 2 and 3) that annealed with both the 5' and 3' regions of the λ R open reading frame. In conjunction a fragment of a plasmid (pKD3) encoding the cat gene selectable marker and FRT site (scar sequence) was isolated as an approximately 1.2 kb Hind III fragment (cat, chloramphenicol acetyltransferase, $Cm^R$) (Datsenko and Wanner 2000). Mixed template PCR was performed using both fragments to produce a fragment suitable for one-step inactivation of E. coli chromosomal genes (Sequence ID No's 4 and 5). The primers additionally contained 5' non-templated sequences identical to the L-Arabinose (araBAD: araB, ribulokinase; araA, arabinose isomerase; araD, ribulose-5-P-epimerase) regulatory region such that recombination placed the fragment into the chromosome in place of parts of the first gene of the arabinose operon, araB (FIGS. 1 and 2, chromosomal, araB::λR::CAT). The final PCR fragment consists of the λ R gene (or alternatively λ SR genes), two FRT scar sequences flanking the cat gene, with araC and araA sequences at the 5' and 3' ends. An alternative method of construction would be to use fragments from pKD4 that uses the kan gene encoding kanamycin resistance in place of the cat gene (Genbank accession numbers: AY048743).

The fragment was transformed into highly competent JM109 or BL21 strains grown in the presence of saturating arabinose of about 0.2% or 3 mM. The parental strain also carried a plasmid pKD46 which encodes an arabinose inducible phage λ Red recombinase system (or pKD20). The plasmid increases the rate of recombination of the linear fragment sufficiently to allow targeted gene inactivation. Transformants, typically tens to about one hundred are selected on chloramphenicol plates (25-150 ug/ml). Diagnostic primers (Sequence ID No.'s 4-12, Table 3) were used to confirm the correct genomic structure of recombinants.

The arabinose operon is subject to both positive and negative regulation (Smith et al. 1978). The presence of arabinose in the culture media stimulates synthesis of the arabinose catabolic enzymes B, A, and D from the $p_{BAD}$ promoter. This requires the araC arabinose-binding protein, the catabolic activator protein CAP, and cyclic AMP (cAMP) together with RNA polymerase. This regulation is utilized in the gene replacement and final induction of λ R endolysin (or λ SR).

The recombination event in the parental strain places the λ R endoolysin gene under the tight control of the arabinose promoter (Datsenko and Wanner 2000). Arabinose becomes a non-metabolizable inducer. Expression of λ R endolysin from this single copy gene can be induced by addition of arabinose into the growth medium. Addition of concentrations of magnesium of about 1 mM, or other similar metals can be used to stabilize the bacterial cell wall to further control lysis, until the freeze-thaw step. In addition the arabinose promoter belongs to a group of catabolic promoters responsive to additional control by the CRP/cAMP complex, which makes the strains suitable for growing in media systems that preferentially induce catabolic responsive promoters (Botsford, J. L. et al. 1992).

Counterselection using plasmid based FLP recombinase (pCP20, temperature sensitive, ori, FLP recombinase) and elevated temperatures allows removal of the cat antibiotic resistance gene with the introduction of a scar site (Cherepanov and Wackernagel 1995). This allows the engineered strain to retain only the λ R gene (or λ SR) and maintains future use of the chloramphenicol marker, or other markers. Each strain can be further engineered as desired using the one-step chromosomal gene replacement method in serial steps of integration and counter selection, or by P1 phage transduction.

The strains represented by embodiments of the present invention were grown in Luria broth (LB) with arabinose to assess the ability to rapidly undergo controlled lysis upon a single freeze-thaw cycle. Arabinose was added to saturation at the beginning of incubation (about 0.2% final concentration). The XJa strain grew well to a density of approximately half that of the parental JM109 strain. This was satisfactory given the inherent toxicity of λ R endolysin and that the induction was prolonged from the time of the start of the bacterial culture. Normally the λ R endolysin works in conjunction with the λ S holin gene to mediate lysis, but in a preferred embodiment of the invention the λ S gene is not expressed and is not necessary. The λ S protein permeabilizes the inner membrane and promotes access of λ R to the pepitdolglycan cell wall. It is contemplated that further regulation of the λ S gene product may offer additionally control over the autolysis event.

In representative cultures about 75% or more of all cells, expressing λ R endolysin, were lysed after one freeze-thaw cycle. The ability to be lysed remained high starting at about 4 hours after induction with arabinose, or from logarithmic growth for approximately 20 additional hours, which is well into stationary phase growth. This corresponds to growth stages where *E. coli* strains are typically harvested for production of recombinant protein. In similar arabinose induction assays the JM109 or BL21 parental strain lysed at abour 10-20% at all stages of growth examined.

The strains of the present invention were lysogenized using the commercially available T7 RNA polymerase based DE3 phage system. This system introduces a single copy of the gene encoding T7 RNA polymerase into the *E. coli* chromosome under control of the lacUV5 promoter. This make the strains be under T7 RNA polymerase regulation for use in the expression of recombinant proteins (see Table 1)(Studier, et al. 1986, Studier, et al. 1990, Novagen Corp.). The bacteriophage T7 RNA polymerase gene and expression system is subject to U.S. Pat. Nos. 4,952,496; 5,693,489; 5,824,528; 5,830,694; and 5,869,320, all of which are incorporated by reference (Brookhaven National Laboratories). There are also foreign equivalent patents covering the T7 gene and system. Stains of the present invention alone or with the λ (DE3) lysogen were assayed using traditional or commercially available chemical buffer lysis protocols (Novagen Corp). The sonication mediated lysis was used as a control for complete lysis. The XJa and XJb *E. coli* strains released comparable amounts of both total protein and enzyme activity as assayed by release of His-tagged β-galactosdase expressed from a plasmid (Studier et al. 1990, Novagen Corp., pet15b, β-galactosideas, Davies and Jacob 1968). The chemical buffer mediated lysis released less protein and showed reduced enzymatic activity. This may be due to the fact β-galactosidase acts as a tetramer with a subunit size of 112 kDa (1,023 amino acids). Protein produced by all the methods was suitable for affinity chromatography. However, about fifty times more starting material was required with the chemical buffer lysis method, likely due to inefficient extraction of the relatively large β-galactosidase protein. In addition prolonged incubation in the chemical buffer at room temperature of about 25° C. resulted in observable degradation of the protein samples.

The use of *E. coli* strains and methods of the present invention provide a novel controlled autolysis phenotype that is evident upon a single freeze-thaw cycle. The methods are rapid and reproducible and save significant sample handling time as well as reducing the overall cost. In addition the system allows the elimination of chemicals such as detergents and salts that may interfere with further analysis of the recombinant proteins. The method is also scalable and compatible with most buffer systems traditionally used in the art or that are commercially available.

DEPOSIT

Four strains described as embodiments of this invention are commercially available to the public (XJa, XJb, XJa (DE3), and XJb (DE3)(Zymo Research Corp).

BRIEF DESCRIPTION OF THE FIGURES

A detailed description of the preferred embodiments is provided herein below with reference to the following drawings.

DETAILED DESCRIPTION OF THE PREFERRED EMBODIMENTS

The disclosure describes rapid and efficient methods for bacterial lysis using engineered *E. coli* strains expressing a chromosomally integrated λ R endolysin gene (or λ SR) under arabinose regulatory control. Bacterial strains are induced by growth in the presence of the non-metabolizable inducer arabinose to undergo controlled autolysis after a single freeze-thaw step. Although traditional methods are available to break-open bacterial cells, including multiple freeze-thaw cycles, French press, lysozyme digestion, or chemical lysis with detergent and/or strong alkali salts, none of these methods offers the desired features of a simple, efficient, economical, and importantly gentle autolysis of *E. coli*.

The following description is of the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 2:
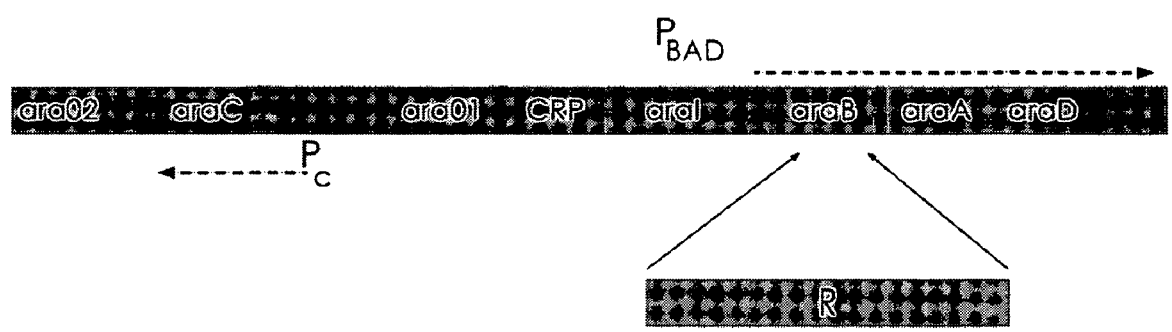
FIG. 2. Depicts the L-arabinose operon with a blow up of the XJa λ R gene inserted according to the method depicted in FIG. 1 (araB::λR).
Figure 3:
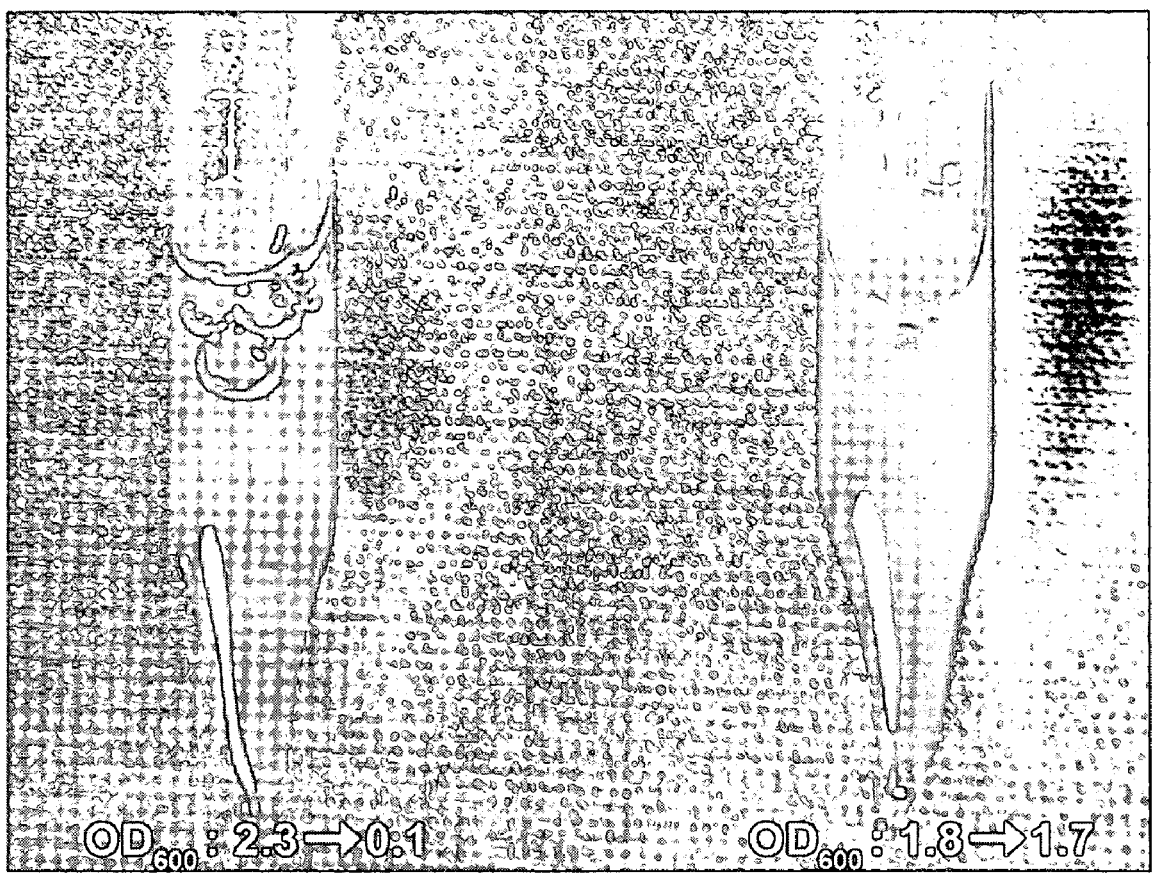
FIG. 3. Autolysis of XJa cells compared to the parental JM109 parental strain after growth in saturating arabinose of about 3 mM and one freeze-thaw cycle.

The representative *E. coli* XJ autolysis strains of the present invention were engineered to address persistent problems associated with efficient bacterial lysis. While there are many methods available to scientists, unfortunately none of these common methods combine all of the ideal features of a simple, efficient yet economical, and gentle method for lysis of *E. coli*, or other bacterial cells. Preferred expression of a chromosomally encoded bacteriophage λ R endolysin (or SR genes) under the arabinose operon's $P_{BAD}$ promoter control (also sometimes known as λ lysozyme), is induced during growth (FIG. 2). Cells are harvested intact while the peptidoglycan layer of the cell walls has been protected from digestion by the cytoplasmic membrane. The membrane is, however, amenable to disruption by a brief physical-chemical stress such as that mediated by a single freeze-thaw cycle after harvesting the cells (FIG. 3). The λ R endolysin is them able to swiftly facilitate degradation of the cell wall to mediate lysis.

Additionally, bacterial and bacteriophage encoded lytic genes, preferably lytic transglycoslylases, expressed by inducible genomic promoters such the arabinose operon $P_{BAD}$ promoter, are contemplated as embodiments of the present invention. These include, but are not limited to enzymes capable of degrading mureine by cleaving the β-1,4-glycosidic bond between N-acetylmuramic acid and N-acetylglusosamine in the peptidoglycan of the bacterial cell wall. Included in this class are the true lysozymes such as the T4 or P22 bacteriophage enzymes as well as those encoded by bacteria, such as the genus *Salmonella*. The expression from the arabinose operon $P_{BAD}$ promoter of related lysozyme genes (mureine hydrolysaes) from bacteria and bacteriophages are additional embodiments of the invention. Also the lytic genes of the well studied phages T4, φX174, MS2, and T7, as well as their close relatives, are all considered as alternative embodiments of the present invention (Young 1992).

Specific genes that are considered to function similarly to the λ R gene and are embodiments of the present invention include, but are not limited to the putative product from the *E. coli* YfhD gene (Genbank P30135), the bacteriophage T7 gp 16 gene (Genbank P03726), the bacteriophage VP7 PRD1 gene (Genbank, P27380), the product of the *E. coli* YafG gene (Genbank, X60739), the tributyltin chloride (TBTCl)-resistance-conferring protein (TBTA) from *Alteromonas* (Genbank D16369)(Koonin and Ridd 1994; Holtjre, et al. 1975, J. Bacteriol. 124: 1067-1076; Mett et al. 1980, J. Bacteriol 144: 45-52; Fukagawa et al. 1993, 194: 733-740). The TBTA protein sequence has been reported to the Swissprot database with two corrections of apparent frameshift mutations (Swissprot P32982 and P32820). Also, The *E. coli* soluble lytic transglycosylases including, but not limited to, the three described slt gene products (Genbank P03810), the 65 kDa (slt70, soluble lytic murein transglycosylase precursor), the 35 kDa (soluble), and 38 kDa (membrane bound form) enzymes are preferred embodiments of the present invention (Engel et al. 1991). Additionally, other bacteria, or microorganisms known in the art encode similar lytic transglycolysase enzymes that have catalytic sit domains or putative sit domains and would function similarly to λ R in the present invention are additional embodiments of the present invention. The most conserved sit domains contains two conserved serines and a glutamate that are part of the domain's active site signature (Thunnissen et al. 1994; Thunnissen et al. 1995).

The rapid autolysis method of the present invention is highly efficient and takes only about a minute (unlike traditional multiple freeze-thaw cycles, or other procedures). It can be applied to any number of samples without a significant increase in processing time or labor (unlike French press or sonication), is reliable and repeatable (unlike lysozyme treatment), and finally, is fully compatible with a wide range of buffers and systems. Additionally, it does not require use of any expensive equipment or the introduction of potentially interfering components such as detergents, or strong salts commonly found in various lytic buffers.

XJ Strain Construction

The lysis of *E. coli* by the λ bacteriophage lytic genes has been well studied and characterized. There are three genes contained in the EcoRI-ClaI $SRR_z$ gene cluster λ. The R gene encodes λ endolysin and is a soluble transglycosylase that cleaves the peptidoglycan of the cell wall (Young et al. 1992; Bienkowska-Szewczyk et al. 1981). The λ R endolysin in principle functions differently from true lysozymes (*Salmonella*, T4, among others) generating cyclic 1,6-disaccharide products, and if inactivated no lysis is evident, though cells still die (Bienkowska-Szewczyk et al. 1981). However, both are typically to be considered mureine hydrolyases, though technically λ R is distinct in the functional mechanism.

The λ S gene is an inner membrane protein that functions to release intracellular accumulation of R endolysin allowing access and attack of the peptidoglycan of the cell wall. The $R_z$ gene is relatively uncharacterized and its function is not essential for lysis of laboratory E. coli strains. The characteristics of λ S and R gene products coupled to improved engineering techniques make them amenable for constructing a chromosomally regulated cassette that can be used to mediate controlled lysis, referred to herein as "autolysis". Further embodiments contemplate placing the lytic enzymes from a variety of organisms known in the art capable of digesting bacterial cell walls under regulatory control of the arabinose $P_{BAD}$ promoter.

E. coli strain engineering methods based on yeast systems provide convenient one-step methods for gene inactivation or replacement (Datsenko and Wanner 2000). This greatly improves the ease of strain construction allowing the use of PCR based targeted gene replacement methods that can place desired genes under control of well characterized inducible E. coli operons, such as the L-arabinose operon $P_{BAD}$ promoter, among others (Smith and Schlief 1978). It also eliminates the need for plasmid borne regulation that is often problematic and less stable.

The arabinose operon is subject to both positive and negative regulation (Smith and Schlief. 1978). The presence of arabinose in the culture media stimulates synthesis of the arabinose catabolic enzymes B, A, and D from the $P_{BAD}$ promoter. This requires the araC arabinose-binding protein, the catabolic activator protein CAP, and cyclic AMP (cAMP) together with RNA polymerase. This regulation is utilized in the gene replacement and final induction of λ R endolysin, or the tandem λ SR cassette.

The λ phage Red recombinase system encodes three genes γ, β, and exo and has been adapted for efficient targeted recombination in E. coli. The λ Red genes have been placed under arabinose control to increase their expression and also enhance the inefficient recombination of linear DNA molecules in E. coli. This inefficiency is primarily due to the E. coli RecBCD recombination pathway's significant exonuclease activity. The one-step system allows straight forward strain construction (Datsenko and Wanner 2000). The method has been used to construct numerous E. coli gene deletions by amplification and transformation of the resistance cassettes— the desired selectable marker flanked by short direct repeat FRT sequences (pKD3: cat, chloramphenicol resistance, $Cm^R$; or pKD4 and pKD13: kan, kanamycin resistance, $Km^R$). When used in conjunction with plasmid based yeast FLP recombinase (pCP20, or similar plasmids) the selectable marker gene is removed via site specific recombination between the FRT sites leaving a scar sequence consisting of the two priming regions, the two FRT sites, and 10 bp between the FRT sites, or an about 82-85 nt region (Cherpanov and Wackernagel, 1995). This scar region allows a new gene target to recombine into the scar sequence allowing multiple rounds of engineering and maintains the future use of the antibiotic marker. The recombination between FRT sites in the same chromosome will lead to deletion or inversion of a large chromosomal segment depending on the orientation of the FRT sites. Thus, when integrating a cassette into a second gene it is advisable to place the second cassette in the same orientation as the first. Alternatively, standard P1 phage transduction (or electroporation) crosses can be used to further engineer the E. coli strains from single mutants (Sternberg et al. 1994, MacCaren and Clark 1996).

There are four basic steps to the gene replacement procedure: 1. PCR amplification of FRT-flanked resistance gene coupled to the gene of interest (if replacement is desired), with non-templated E. coli target sequences at the ends (from amplification primers); 2. Transformation of the parental E. coli strain expressing λ Red recombinase; 3. Selection of antibiotic resistant transformants; 4. Elimination of the resistance marker gene using a FLP expression plasmid. The structural fidelity of transformants at step 3 and 4 can be monitored via PCR with specific diagnostic primers to each genomic locus. The last step of elimination of the antibiotic resistance marker can be optional. If the antibiotic marker is present it offers a convenient method to monitor the strain, however this precludes using plasmids carrying that selectable marke, or use in further strain construction (FIG. 1).

The araB::λR and araB::λSR Construction

Figure 1:
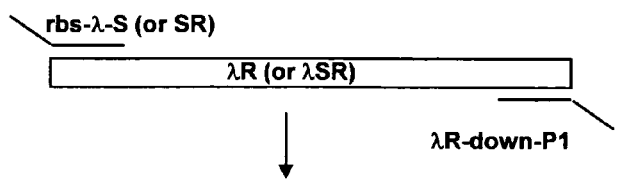
FIG. 1. The scheme for construction of XJ *E. coli* strains is depicted in Steps 1-4. Step 1: The λ R (or SR) genes were amplified by PCR from *E. coli* (WT) 533 containing a wild-type λ lysogen. Step 2: Mixed PCR with a fragment of pKD3 provided the final product consisting of joining the λ lysis genes (λ R, or λ SR) to the cat gene and addition of the arabinose operon araC and araA sequences onto each end of the fragment for directed recombination into the *E. coli* genome. Step 3: The fragment was transformed into highly competent JM109, or BL21 cells carrying pKD46 (arabinose controlled λ Red recombinase system), $Cm^R$ transformants were selected that replace a portion of araB and is under control of the $P_{BAD}$ promoter in single copy (λ R or λ SR) gene. Step 4: The final step of recovery of the cat selectable marker by excision with FLP recombinase (pCP20) selects for $Cm^s$.
Figure 1:
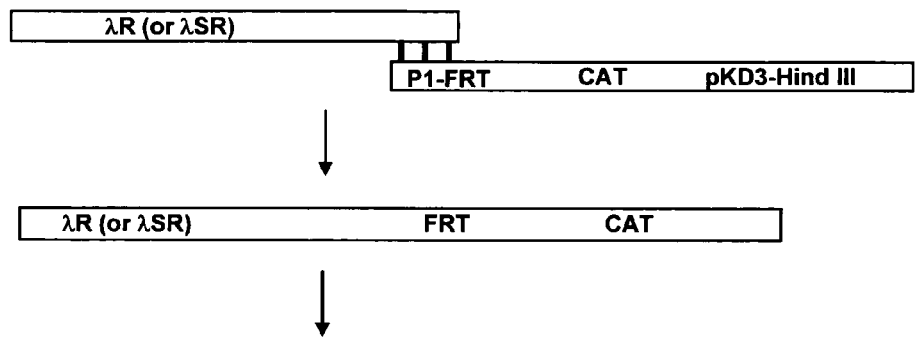
Figure 1:
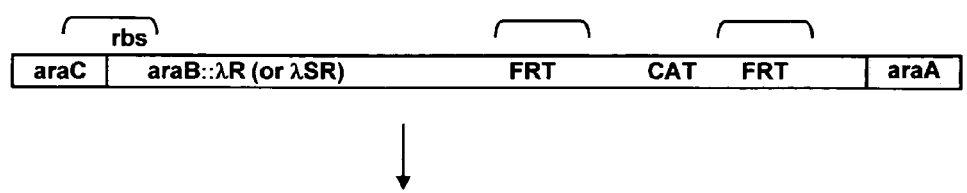
Figure 1:
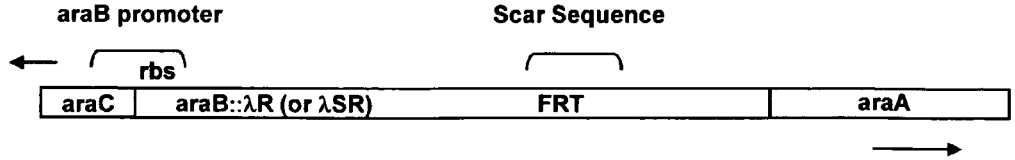

The λ R (or SR) cassettes were generated via PCR based techniques known by practitioners in the art (FIG. 1). The approximately 1.2 kb piece of pKD3 was isolated for use as one template (genbank accession number AY048742). In addition chromosomal DNA was isolated from a wild-type (WT) E. coli strain 533 containing a WT λ lysogen in the chromosome as the second template. Two separate PCR reactions using primers indicated in Table 2 generated the expected sized fragments each that amplified either the λ R or λ S genes. The annealing temperature was about 65° C. with 30 rounds of amplification and standard conditions known in the art for each reaction.

TABLE 1

First PCR Reaction expected sized fragments

| Primer 1 (Sequence ID No.) | Primer 2 (Sequence ID No.) | Template | PCR Product |
|---|---|---|---|
| rbs-λS (Seq ID No. 1) | λ-down-P1 (Seq ID No. 3) | E. coli $λ^{wt}$ chromosome | 842 bp |
| rbs-λR (Seq ID No. 2) | λ-down-P1 Seq ID No. 3) | E. coli $λ^{wt}$ chromosome | 542 bp |

The PCR λ derived products listed in Table 2 were mixed at an approximately equal molar ratio with the pKD3 Hind III fragment, consisting of the cat gene, flanked by FRT sequences. The λ-down-P1 primer (Seq ID No. 3) contains a P1 sequence that allows overlap with the pKD3 Hind III fragment. A second round of mixed template PCR using standard reaction conditions with an annealing temperature of 650 and 30 rounds of amplification was performed. In addition to joining the λ lysis genes (λ R, or λ SR) to the cat gene the PCR reaction adds the arabinose operon araC and araA sequences onto each end of the fragment for directed recombination into the E. coli genome (FIG. 1).

The JM109 (XJa progeny) or BL21 (XJb progeny) strains carrying the pKD46 (ampicillin, $Cm^R$) encoding the λ Red recombinase system, were made ultra competent using standard techniques known in the art and commercially available (Smith et al. 1990, Zymo Research Corp.). The strain was grown at about 25° C.-30° C. and aliquots were either used fresh or after storage at −70° C. The pKD46 plasmid contains a tL3 terminator and typically generates more transformants, compared to a similar pKD20 plasmid (Genbank accession numbers AY048746 and AY048745, respectively). The primers, templates and sized fragments from typical mixed template PCR reactions are shown in Table 3.

TABLE 2

Expected PCR Fragments From Mixed Template Reactions

| Primer 1 (Seq ID No.) | Primer 2 (Sq ID No.) | Template | PCR Product |
|---|---|---|---|
| araB-rbs (Seq ID No. 4) | araA-P2 (Seq ID No. 5) | 842 bp PCR 1 Product (Table 1), plus 1.2 kb pKD3 Hind III fragment fragment | 1925 bp |

TABLE 2-continued

Expected PCR Fragments From Mixed Template Reactions

| Primer 1 (Seq ID No.) | Primer 2 (Sq ID No.) | Template | PCR Product |
|---|---|---|---|
| araB-rbs (Seq ID No. 4) | araA-P2 (Seq ID No. 5) | 542 bp PCR 1 Product (Table 1), plus 1.2 kb pKD3 Hind III fragment | 1625 bp |

The strain was grown in the presence of saturating arabinose of about 0.2% final concentration to induce expression of λ Red recombinase. The λ R (or λ SR) gene replacement cassette (described below) was transformed by electroporation followed by prolonged (10-20 h) outgrowth at 25° C. or 30° C. in SOC containing 20 mM MgCl$_2$ to allow recovery of the cells. The magnesium is important to enhance survival of the cells that may transiently express the lysis genes, especially for the λ SR construct. Transformations generated from 10-100 transformants in standard reactions using about 1-2 ug of linear fragment. Selection for recombination into the *E. coli* genome was on chlormamphenicol containing LB media (25-150 ug/ml) supplemented with 20 mM MgCl$_2$ at 25° C. and 30° C. The presence of high levels of magnesium stabilizes the bacterial cell wall (calcium and other divalent metals can also be used). The temperature of outgrowth did not significantly affect the overall numbers or the fidelity of successful recombination events. Individual Cm$^R$ transformants were streaked for single colonies and incubated at 37° C. on LB with no antibiotic. Colonies were tested for Amp$^S$ (loss of pKD46) and Cm$^R$ (λ R or λ SR cassette integration in genome). Candidate strains were grown at 37° C. in LB plus 50 ug/ml chloramphenicol and frozen at −70° C. These can be used for phage P1 transduction to generate additional strains in lieu of the one-step gene inactivation or replacement procedures.

Each positive Cm$^R$ clone as well as their progeny was assayed via diagnostic PCR for the expected genomic structure using the primers in Table 3. Candidates that did not show the expected sized fragments were discarded and positive candidates were further assayed for general growth characteristics. The set of strains name XJa are derived from JM109 and those named XJb are derived from BL21 (Table 4). Each strain contains the cat gene in their genome from the integration of the λ R cassette.

Candidate strains were made ultra competent by standard techniques and transformed with pCP20 encoding the yeast FLP recombinase under λ$_{PR}$ promoter under control of the cI857 repressor (Cox et al. 1983). Transformants were selected on LB containing ampicillin (100 ug/ml) at 37° C. Further embodiments of the invention entail strains in which the marker has been removed making them Cm$^S$, and allowing use of the chloramphenicol antibiotic resistance marker for plasmids or other strain modifications (Example 3). In addition the XJa and XJ b strains were lysogenized with the λ DE3 phage to make them competent to express proteins using the T7 RNA polymerase system (Studier et al. 1990; Novagen Corp.; Example 4).

TABLE 3

Diagnostic PCR Fragments

| Primer 1 (Seq ID No.) | Primer 2 (Seq ID No.) | araB::λR::CAT cat inserted | araB::λR cat Δ | araB::λSR::CAT cat inserted | araB::λSR cat Δ |
|---|---|---|---|---|---|
| araB-up Seq ID No. 6 | λR-up Seq ID No. 7 | 567 bp | 567 bp | 567 bp | 567 bp |
| araB-up Seq ID No. 6 | C1 (pKD3) Seq ID No. 10 | 897 bp | none | 1198 bp | none |
| λR-down Seq ID No. 8 | C1 (pKD3) Seq ID No. 10 | 305 bp | none | 305 bp | none |
| λR-down Seq ID No. 8 | araA-down Seq ID No. 9 | 1474 bp | 544 bp | 1474 bp | 544 bp |
| C2 (pKD3) Seq ID No. 11 | araA-down Seq ID No. 9 | 459 bp | none | 459 bp | none |
| araB-up Seq ID No. 6 | araA-down Seq ID No. 9 | 2066 bp | 1136 bp | 2367 bp | 1437 bp |

TABLE 4

*E. coli* strains expressing λ R Endolysin from the araB P$_{BAD}$ promoter

| Strain Name | Parental Strain | Genotype |
|---|---|---|
| XJa | JM109 | *E. coli* K recA1 supE44 endA1 hsdR17 (r$_k$$^-$, m$_k$$^+$) gyrA96 relA1 thi mcrA Δ(lac-proAB) ΔaraB::λR, cat F'[traD36 proAB$^+$ lacI$^q$ lacZΔM15] |
| XJa(DE3) | JM109 | *E. coli* K recA1 supE44 endA1 hsdR17 (r$_k$$^-$, m$_k$$^+$) gyrA96 relA1 thi mcrA Δ(lac-proAB) ΔaraB::λR, cat F'[traD36 proAB$^+$ lacI$^q$ lacZΔM15]λDE3 |
| XJb | BL21 | *E. coli* B F$^-$ ompT hsdS$_B$(r$_B$$^-$ m$_B$$^-$) gal dcm$^+$ araB::R, cat |
| XJb (DE3) | BL21 | *E. coli* B F$^-$ ompT hsdS$_B$(r$_B$$^-$ m$_B$$^-$) gal dcm$^+$ araB::R, cat λDE3 |

Autolysis Overview

The autolysis procedure can be used for extraction of intracellular material, including proteins, nucleic acids, or any other component. One preferred embodiment is described for a small 2 ml final culture volume and can be modified proportionally in other embodiments according to needs for larger amounts of cell material. Antibiotics are used when required for plasmid selection. Chloramphenicol can not be used for selection for the XJ autolysis cells since they contain the chloramphenicol acetyltransferase (cat) gene inserted on the chromosome. Cells are generally grown at 37° C. but lower temperatures can be used as well.

XJa or XJb cells at any stage can be used to prepare a starter culture. To withdraw cells from the glycerol stock vial, remove a little of the material from the top of the frozen culture and return the tube back in the freezer promptly. Streak the cells on LB agar plates and incubate overnight. Prepare starter culture by inoculating one bacterial colony into 1 ml of Luria Broth (LB) and growing for about 16 hours (overnight). Other media can be used as well. In order to induce λ R endolysin, add about 100 ul of saturated starter culture into final 2 ml of LB broth containing about 3 mM of arabinose final concentration, with 1 mM $MgCl_2$. Cells can be grown as needed for the particular application. A concentrated arabinose solution that is convenient to use is 1.5 M L-arabinose and 0.5 M $MgCl_2$ that can be diluted 1:500 to achieve induction. The presence of magnesium at concentration of about 1 mM stabilizes the bacterial cell wall slightly. This aids in preventing premature lysis prior to the freeze-thaw cycle. Magnesium or other metal concentrations above this level may inhibit autolysis to a degree and are preferably avoided. Higher levels of arabinose are saturating and can be used, but are not typically necessary.

Figure 7:
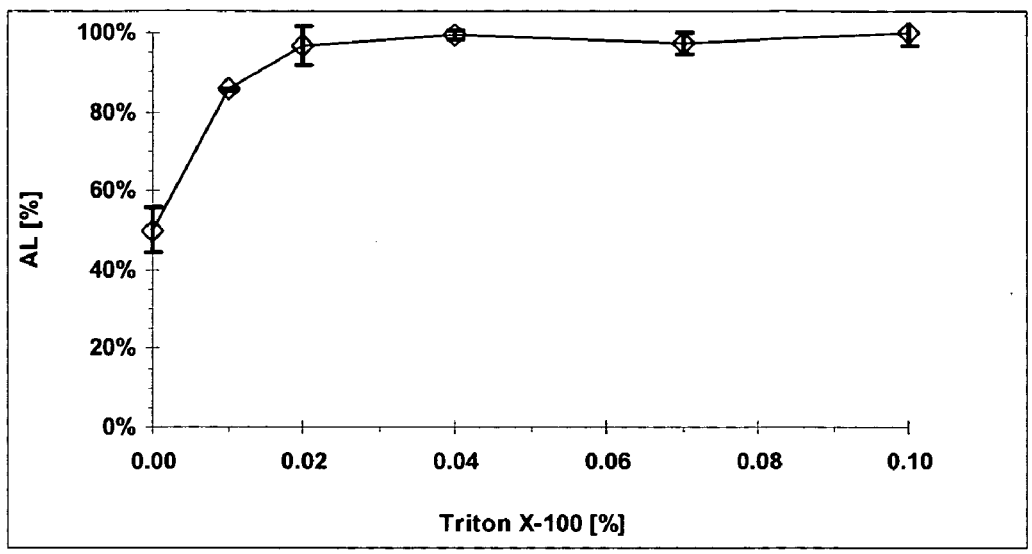
FIG. 7. The effect of Triton-X-100 on the autolysis of the XJa (DE3) *E. coli* strain is shown. A. Percentage of cell lysis reaches a maximum of close to one hundred percent at about 0.02-0.03% Triton-X-100. B. The release of protein approaches about 90% of total cellular protein at about 0.02-0.03% Triton-X-100. Values are normalized to samples that were lysed by sonication, under conditions designed to give complete lysis as assessed by no further release of cellular protein with continued sonication (AL [%]).
Figure 7:
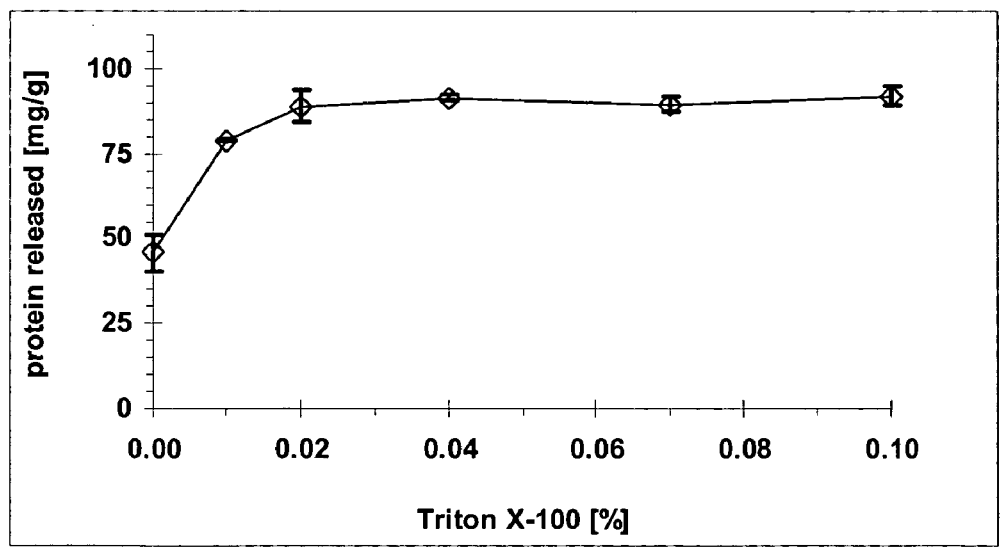
Figure 8:
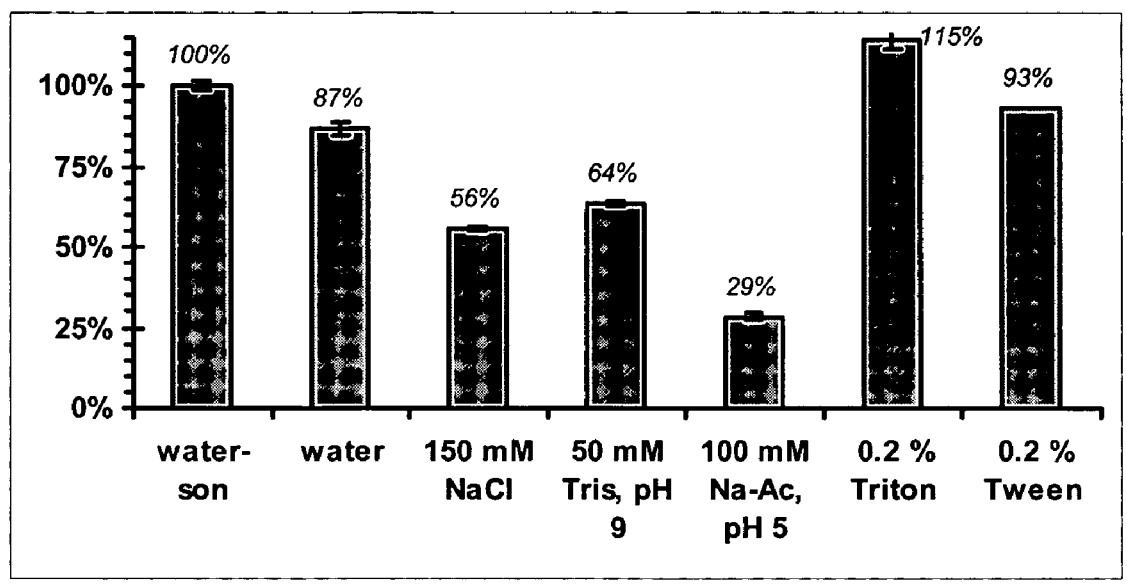
FIG. 8. The effect of adding additional buffer components on the XJa strain's ability to undergo autolysis after one freeze that cycle after induction of λ R with arabinose is shown (0.2%)(Left to to Right: Sonication Control; water; 150 mM NaCL; 50 mM Tris pH 9; 100 mM Na-Ac; 02% Triton-X-100; 0.2% Tween-20). Values are normalized to samples that were lysed by sonication, under conditions designed to give complete lysis as assessed by no further release of cellular protein with continued sonication (AL [%]).

The autolysys method is compatible with many detergents if their use is desired to augment lysis and recovery. If the results obtained are not optimal, lysis can be improved by inclusion as little as 0.01% Triton-X-100 in the buffer (Sigma). Triton-X-100 and Tween-20 are both suitable for use with the present invention. However Triton at about 0.02-0.03% is typically sufficient to maximize recovery and works slightly better than other detergents (FIG. 7). Note increasing detergent levels up to about 10 fold beyond 0.02-0.03% does not significantly increase lysis (FIG. 8). Buffers typically used for $Ni^{2+}$ chromatography, such as His-binding buffers can be used to lyse both XJa and XJb cell pellets (Studier 1990; Novagen Corp.; Zymo Research Corp). Lysis will also improve by incubating the cells at higher temperatures (25-37° C.) or for longer time (10 or 20 minutes) after thawing.

For the best results, cells should not be growing actively prior to arabinose induction. This is achieved by using an overnight starter, where cells are already in the stationary growth phase, as directed above. If a fresher starter needs to be used, include arabinose in the starter culture.

Harvest cells and resuspend in about 500 ul of buffer of that is suitable for downstream assays. Acidic buffers and buffers containing higher concentrations of $Mg^{2+}$ (>1 mM)(or calcium), and related metals that stabilize cell walls, inhibit the lysis reaction to varying degrees. If necessary, add magnesium to the buffer after cells are lysed if $Mg^{2+}$ is required for activity in downstream assays.

In should be noted that XJb lysis efficiency is about 10-20% lower compared to XJa. To achieve optimal lysis, more care needs to be taken when selecting a specific lysis buffer. In order to lyse the cells resuspend the cell pellet and put the sample through one freeze-thaw cycle. Cells will be lysed at this point. A centrifugation step can be used to obtain a cell free extract (CFE).

Depending on the amount of material used, the lysed material may become viscous, preventing efficient manipulation. However, for most routine applications it is not necessary to use a large amount of cell material. If necessary, vortexing vigorously for 30 seconds will decrease viscosity in most cases, or sonication can also be used if larger amounts of material is being used (Deininger, 1983; Hengen P. N., 1997). Alternatively, a nuclease treatment (e.g. DNAse I) can be used to reduce viscosity. Diluting the cell lysate with additional buffer will also reduce viscosity issues.

Additionally, there are various methods to speed up the freeze-thaw process. A dry ice/ethanol bath or ultra-cold isopropanol bath will freeze the sample within seconds. A water bath of 10° C. to 37° C. can be used to thaw the samples more quickly.

EXAMPLE 1

Autolysis Phenotype

The strains of the present invention undergo rapid autolysis after a single freeze-thaw cycle. A culture of E. coli XJa cells (I) and control E. coli JM109 cells (II) were grown in LB for 24 hours (FIG. 3). Autolysis was induced by arabinose addition to about 0.2%, or saturating levels during the growth. An aliquot of about 4 mg of wet cells were resuspended in 1 ml of water, frozen on dry ice, and then incubated for 5 minutes in a water bath at 15° C. The OD600 values were measured for each culture and indicate cell density changes before and after the one freeze-thaw cycle. The XJa strain expressing λ R endolysin showed a dramatic reduction in absorbance from OD600 2.3 to 0.1, demonstrating efficient lysis. In comparison the control strain JM109 showed no significant lysis (OD600 1.8 to 1.7). Similar results are obtained with the XJb strains (data not shown).

EXAMPLE 2

Quantification of Autolysis Phenotype

Figure 4:
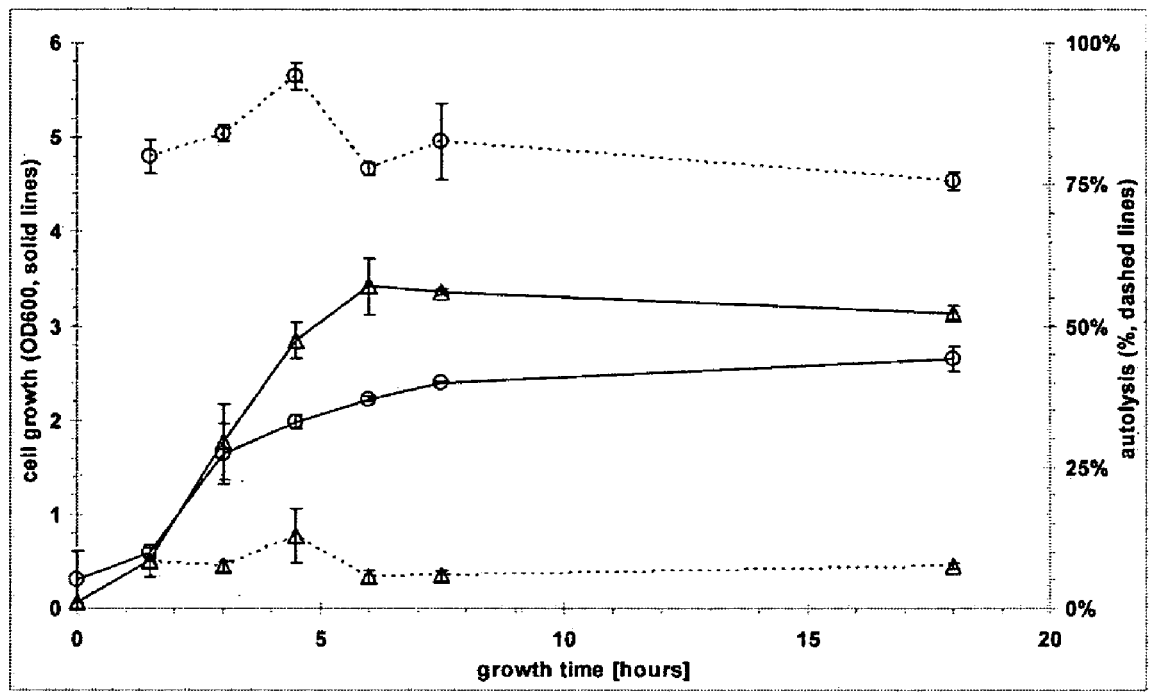
FIG. 4. Autolysis of *E. coli* XJa strain grown in LB media with about 0.2% arabinose added at beginning of incubation. The chart shows the growth (open circle, solid line) and extent of autolysis (open circle, dashed line) of the autolysis strain XJa. For comparison, the growth (open triangle, solid line) and autolysis (open triangle, dashed line) of a control strain, *E. coli* JM109, is shown. The autolysis activity is defined as the amount of cell protein released after one freeze-thaw cycle, compared to the total protein in that sample (% Autoysis, or AL [%]). The total protein was measured by Bradford assay (Pierce) after cell disruption by sonication at conditions which insured complete cell lysis. Similar results are obtained with the XJb strains (not shown).

The autolysis of E. coli XJa strain was examined to quantify the percentage of lysis. Strains of XJa and parental JM109 were grown in LB media with about 0.2% mM arabinose added at beginning of incubation. The cultures were grown for up to 18 hours and samples harvested and assayed by putting them through a single freeze-thaw cycle (FIG. 4). The chart shows the growth (circle XJa, triangle JM109; solid lines) and extent of autolysis (circle XJa, triangle JM109; dashed lines) of the autolysis strain XJa and parental control JM109 strain. The XJa strain expressing λ R endolysin showed that more than 75% of cells lysed compared to less than 5% for the control JM109 strain. In addition the growth of the XJa strain is only slightly reduced compared to the parental JM109 control. Similar overall results are obtained with the XJb strains (not shown).

EXAMPLE 3

Removal of Antibiotic Marker Gene

XJa and XJb strains that are $Cm^R$ and that met the diagnostic PCR criteria that shows the proper genomic structure and that also showed no obvious growth defects can be transformed with pCP20 encoding the yeast FLP recombinase to facilitate removal of the cat gene. This pCP20 plasmid has a temperature sensitive origin of replication (ori) and is lost when cells are grown at 37° C. or higher. Strains can be grown at 30° C. on LB to allow recombination and loss of the cat gene. Single colonies may have to be purified at from 37° C.-42° C. to select for temperature sensitive loss of the pCP20. Selection at 37° C. is not always effective at removing pCP20 and more stringent selection at 42° C. may be necessary to obtain $Amp^S Cm^S$ clones. Candidates can be frozen at −70° C. for further study. Representative strains that have removed the cat gene for XJa and XJb are preferred embodiments of the present invention.

EXAMPLE 4

XJ λ (DE3) Lysogen Construction

The strains of the present invention were lysogenized using a commercially available λ phage (DE3) method to introduce the T7 RNA polymerase system, for use in the expression of recombinant proteins (see Table 1)(Studier, et al. 1986, Studier, et al. 1990, Novagen Corp.). These additional stains are preferred embodiments that couple the autolysis of the bacteria to a well studied protein expression system. XJa and XJb strains were grown supplemented with maltose (0.2% maltose, 10 mM $MgSO_4$). The stock mix of λ DE3 and helper phage were added to cell dilutions. The phage and cell mixtures were incubated at 37° C. for about 20 minutes to allow infection and then plated onto chloramphenicol containing LB plates (25 ug/ml). Candidate lysogens were assayed with tester phage according to the standard protocol. Samples were plated with top agar on LB plates alone or supplemented with IPTG (isopropyl-b-thiogalactopyranoside) to allow for induction of T7 RNA polymesrase. Candidates lysogens were isolated that had low basal expression of T7 RNA polymerase (large plaques on IPTG and small on LB)(Table 4).

EXAMPLE 5

Quantification and Enzymatic Activity of β-Galactosidase Isolated Via Autolysis Extraction of recombinant protein was done from XJa (DE3) and JM109 (DE3) to assay both the quantity and relative enzymatic activity of a marker enzyme in order to assess the efficiency of preferred embodiments. Cultures of XJa (DE3) or JM109 (DE3) expressing a His-tagged β-galactosidase from a pet based plasmid were grown overnight in commercially available EB/OB (expression broth/overexpression broth) media supplemented with about 0.2% arabinose, 1 mM $MgCl_2$ according to the manufacturers instructions (Zymor Research Corp.; Novagen Corp.). The EB/OB media system provides convenient protein expression from the T7-lac promoter by regulating levels of cyclic AMP (cAMP) and cAMP receptor protein. Protein expression is repressed in EB media followed by high level expression in OB media (Zymo Research Corp). The cells were harvested at OD600 5.0 or higher and the weight of the cell material measured. Individual samples were processed by different lysis methods for comparison of protein recovery and activity.

Cell pellets were lysed by putting them through one freeze that cycle in His-binding buffer (Zymo Research Corp). Typical autolysis assays were done with about 2.6 mg wet cells/ml. Parallel samples were lysed to completion using standard sonication procedures with about 10 mg/ml on ice in His-Binding buffer (3 minute cycles with a miniprobe, 3 seconds on, 3 seconds off)(Zymo Research Corp). Additionally, samples were also lysed with a commercially available detergent buffer according to the manufacturer's instructions, 15 minutes at room temperature (Novagen Corp). More cell material was required with this method to obtain adequate amounts of β-galactosidase protein and typically samples were processed at 60 mg/ml.

Figure 5:
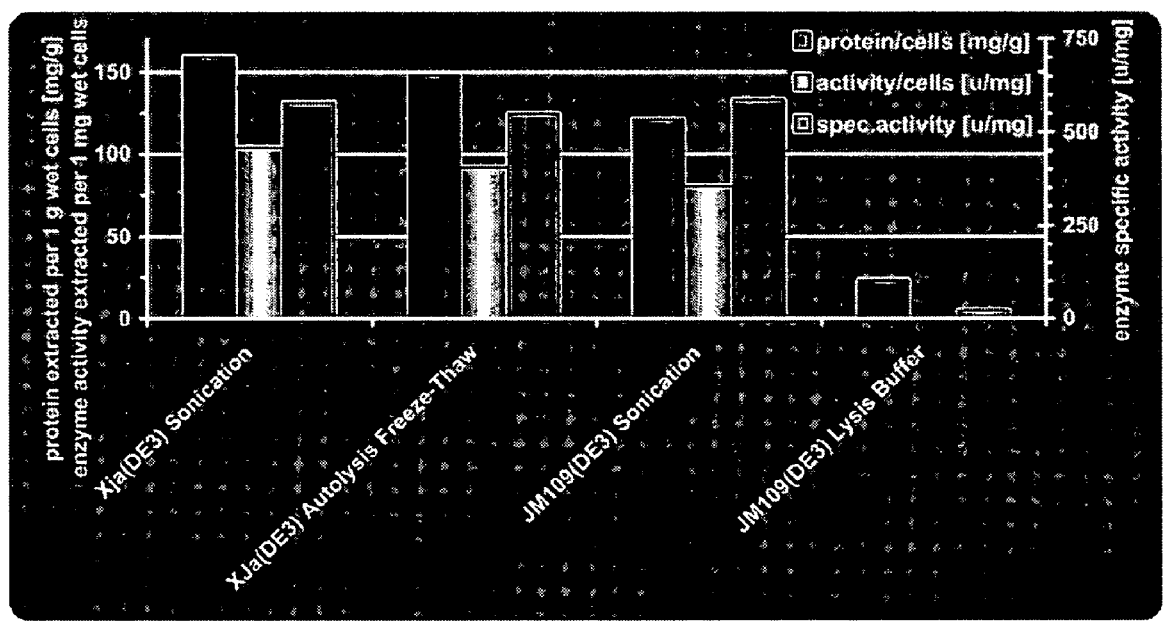
FIG. 5. Shown is a bar graph that shows the comparison of cell free extracts (CFE) prepared from XJa (DE3) and JM109 (DE3) expressing a His-tagged β-galactosidase protein as a marker enzyme. The CFE's were made by autolysis (one-freeze thaw cycle), sonication, and from a commercially available lysis buffer. The total protein extracted from one gram wet cell (mg/g) is shown compared to the activity (ul/mg), and specific activity (units/mg).

The total protein extracted was measured by Bradford assay and compared to the gram weight of cells (FIG. 5). In addition the activity of the β-galactosidase was assayed in a standard ONPG (o-nitrophenyl beta-D-galactopyranoside) assay to determine relative activity of a recombinant enzyme prepared from XJa (DE3) strain (Sambrook and Russell 2001). A typical reaction contained: 5 ul protein sample, 226 ul 0.1M sodium phosphate pH7.5, 66 ul 13 mM ONPG, 2 ul $MgCl_2$, 1 ul β-mercaptoethanol. Reactions were incubated at 37° C. until color developed (time recorded) and then stopped by addition of 1 M $Na_2CO_3$ and measured at 420 nm in a spectrophotometer. One unit activity was defined as 1 unit absorbance increase per minute. After lysis, the released protein and activity were normalized relative to the wet cell weight as is standard in such assays to facilitate comparisons.

The autolysis method and sonication released comparable amounts of both total protein and enzyme activity (FIG. 5A). However, the commercial lysis buffer released less protein and also showed less enzyme activity. This may be due to the requirement for prolonged incubation at room temperature and also by the reagents inefficiency in extracting larger molecular weight proteins. It should be noted that β-galactosidase is active as a tetramer of 1023 aa, or about 112 kDa.

EXAMPLE 6

Comparison of Lysis Methods

Figure 6:
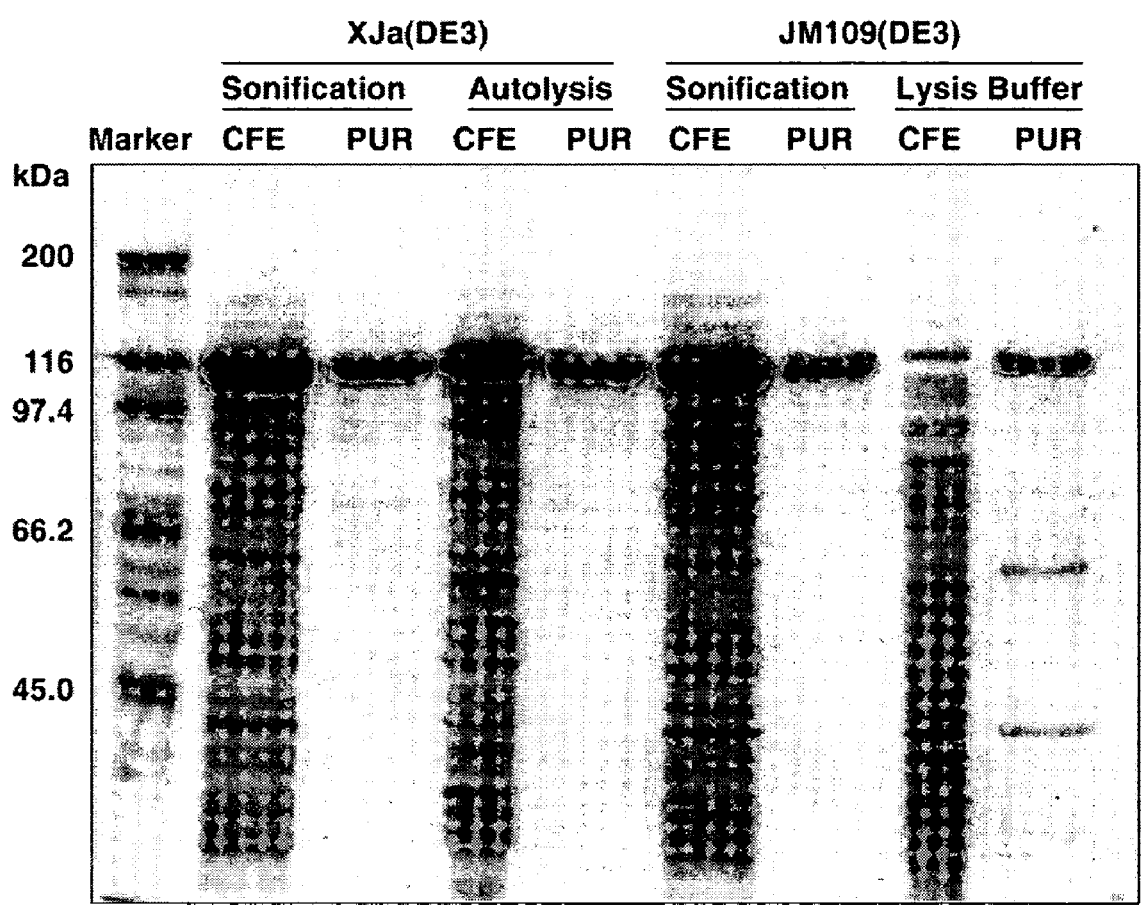
FIG. 6. Shown are samples of His-tagged β-galactosidase cell free extracts (CFE) or the purified protein isolated by $Ni^{2+}$ affinity chromatography (PUR) separated on a 10% SDS-PAGE gel. The CFE's were made from autolysis, sonication, or commercial lysis buffer.

Protein from all three extraction methods used in Example 5 (Autolysis, sonication, commercial lysis buffer) was affinity purified using spin-column $Ni^{2+}$ affinity chromatography from commercially available protocols (Zymo Research Corp). Cell free extracts (CFE) were prepared by the methods described above and the His-tagged β-galactosidase purified according to the manufacturer's instructions (PUR)(See FIG. 6, Left XJa (DE3) Sonication, Autolysis; Right JM109 (DE3) sonication, Commercial lysis buffer). Approximately 15 ug of total or purified protein was loaded for each sample from the three lysis methods (FIG. 6). Protein was separated by electrophoresis in a 10% SDS-PAGE gel.

Protein purification from autolysis derived XJa (DE3) cell free extracts was about 50 times more efficient compared to the commercial lysis buffer. This is likely due to the poor extraction of the relatively large β-galactosidase protein. The protein purified from XJa(DE3) cell free extracts also showed significantly less degradation products compared to those from JM109(DE3) using the commercial lysis buffer (See PUR far right lane). One should note the virtual absence of large molecular weight proteins in the sample derived from the commercial lysis buffer (CFE, second lane from right). This necessitated using 50 fold more total protein to obtain equivalent amounts of purified protein compared to the XJa (DE3) autolysis sample.

EXAMPLE 7

Effect of Triton-X-100 on Autolysis

The XJa (DE3) strain was grown and induced with arabinose at about 0.2% as described previously. The effect of the presence of detergent Triton-X100 was assayed on autolysis in water supplemented with detergent, after induction by putting the sample through one freeze that cycle (FIG. 7). The percentage of cells lysed reached approximately 100% with about 0.02-0.03% of Triton-X-100 in the cell re-suspension buffer (Sigma). The amount of protein released was measured and reached a maximum of about 90% of total cellular protein. Values are normalized to samples that were lysed by sonication, under conditions designed to give complete lysis as assessed by no further release of cellular protein with continued sonication. Thus the presence of low amounts of such detergents can increase the efficiency of the autolysis further.

EXAMPLE 8

Effect of Additional Buffer Components on Autolysis

The XJa (DE3) strain was grown and induced with arabinose at about 0.2%, as described previously. The effect of several commonly used detergents, and buffers components on the degree of lysis of the XJa (DE3) strain was measured. Each cell pellet was resuspended in a buffer containing the particular chemical component and then lysed by a single freeze that cycle and protein release measured to determine lysis. Values are normalized to samples that were lysed by sonication, under conditions designed to give complete lysis as assessed by no further release of cellular protein with continued sonication. The use of the detergent Triton-X-100 (0.2%) gave essentially complete lysis. The detergent Teewn-20 (0.2%) gives the next highest degree of lysis at about 93%, followed by a water (87%), 50 mM Tris pH 9 (64%), 150 mM NaCl (56%), and 100 mM sodium acetate pH 5 (29%). It should be noted that the detergent used in this early experiment was approximately 10 fold that used in other experiments that yielded similar amounts of lysis. Thus there should be no need to add more than the lower amount (0.02-0.03%) of Tween-20 or Triton-X-100 to achieve optimal autolysis. Thus when a lysis buffer contains moderate to high levels of chemical components there is some inhibition of autoysis, but significant autolysis capacity remains.

EXAMPLE 9

Effect of pH on Autolysis with Tris and Phosphate Based Buffers

Figure 9:
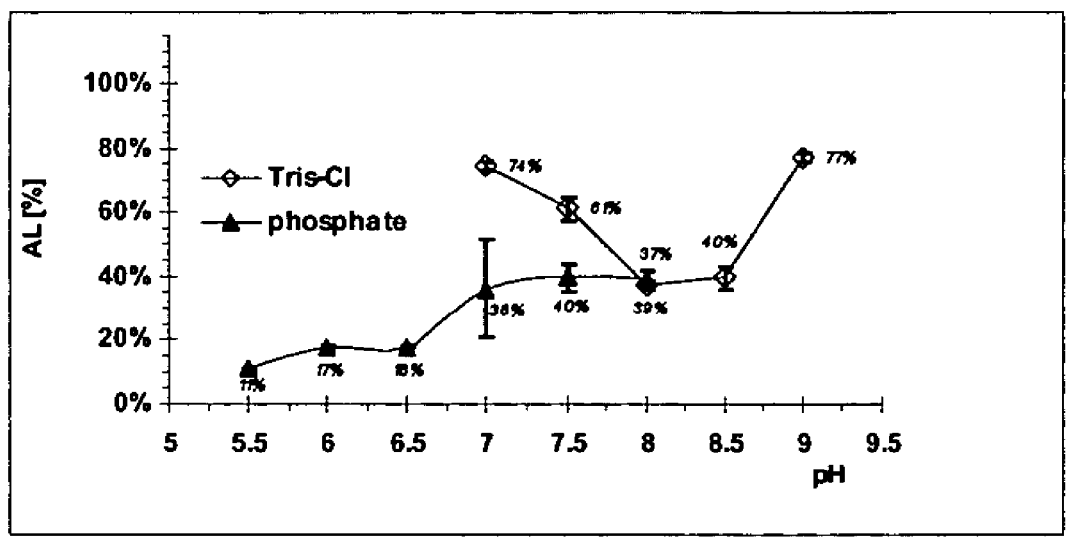
FIG. 9. The XJa (DE3) strain was grown and induced with arabinose at about 0.2%, as described previously. The pH of either a 50 mM phosphate based buffer or 50 mM Tris based buffer from a pH range from 5 to 9, for phosphate and 7 to 8 for Tris-Cl was assayed for the relative percentage lysis as well as the amount of protein released compared to wet weight of cells.
Figure 9:
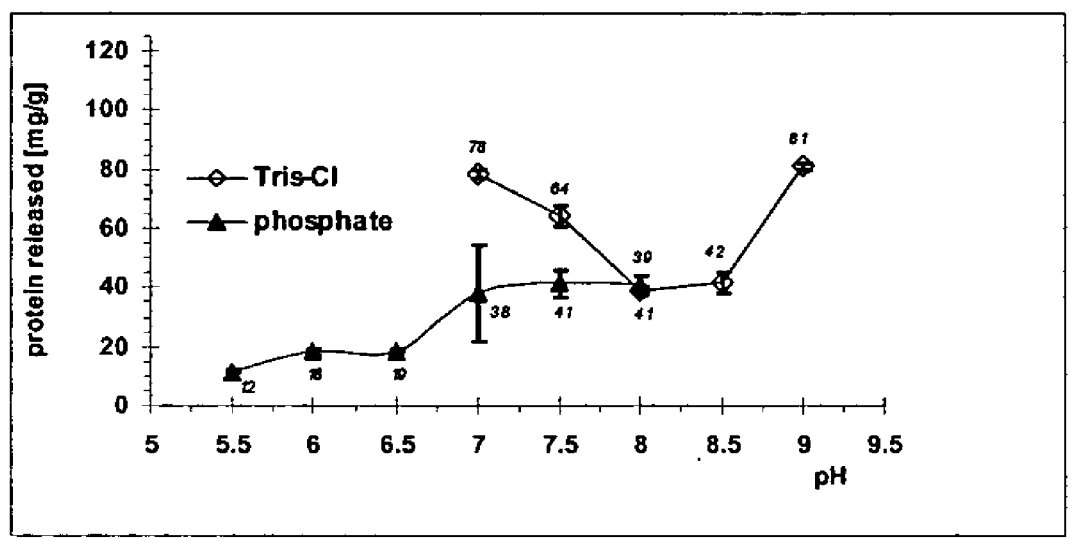

The XJa (DE3) strain was grown and induced with arabinose at about 0.2%, as described previously. The pH of either a 50 mM phosphate based buffer or 50 mM Tris based buffer from a pH range from 5 to 9, for phosphate and 7 to 8 for Tris-Cl was assayed for the relative percentage lysis as well as the amount of protein released compared to wet weight of cells (mg/g)(FIG. 9, open diamonds Tris-Cl; closed triangles phosphate). For the Tris buffer the most significant lysis and protein release was observed at a pH of 7 at 74%/78%, respectively. The amount of lysis and protein release dropped off to about 37%/41% at a pH of 8. The phosphate buffer displayed a gradual increase in lysis and protein release from about 10%/10% at pH 5.5 to about 77%/81% at pH 9.0. Values are normalized to samples that were lysed by sonication, under conditions designed to give complete lysis.

EXAMPLE 10

Effect of Magnesium on Autolysis

Figure 10:
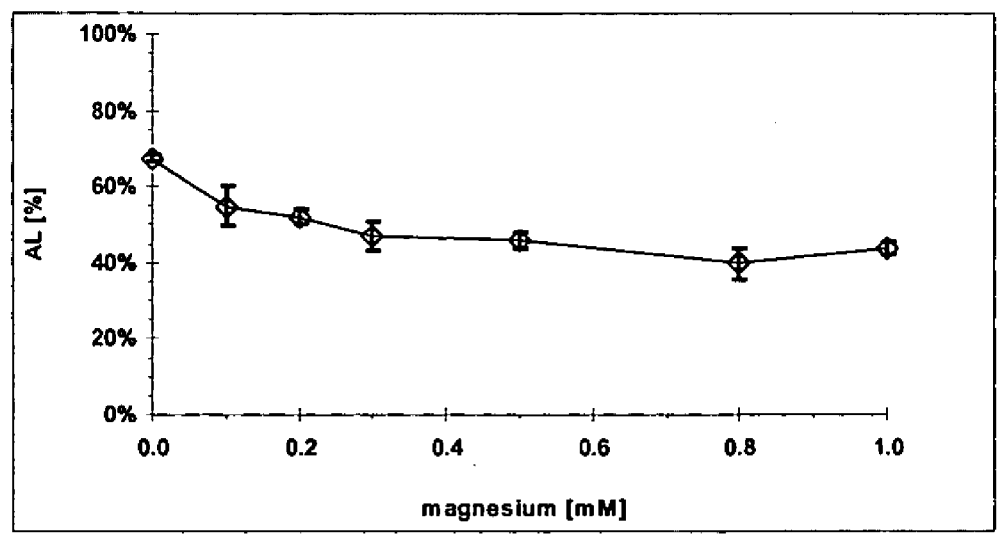
FIG. 10. The effect of Magnesium ion on the ability of the XJa (DE3) to undergo autolysis after one freeze-thaw cycle of the strain is shown after induction of λ R with arabinose is shown (0.2%). The XJa (DE3) strain was grown and induced with saturating arabinose at about 0.2% as described previously. The effect of several commonly used detergents, and buffers components on the degree of lysis of the XJa strain was measured. Each cell pellet was resuspended in a buffer containing the particular chemical component and then lysed by a single freeze-thaw cycle and measured at OD600. The percentage values were normalized to a sonication control under conditions that completely lyse the cells. Values are normalized to samples that were lysed by sonication, under conditions designed to give 100% lysis as assessed by no further release of cellular protein with continued sonication (AL [%]).
Figure 10:
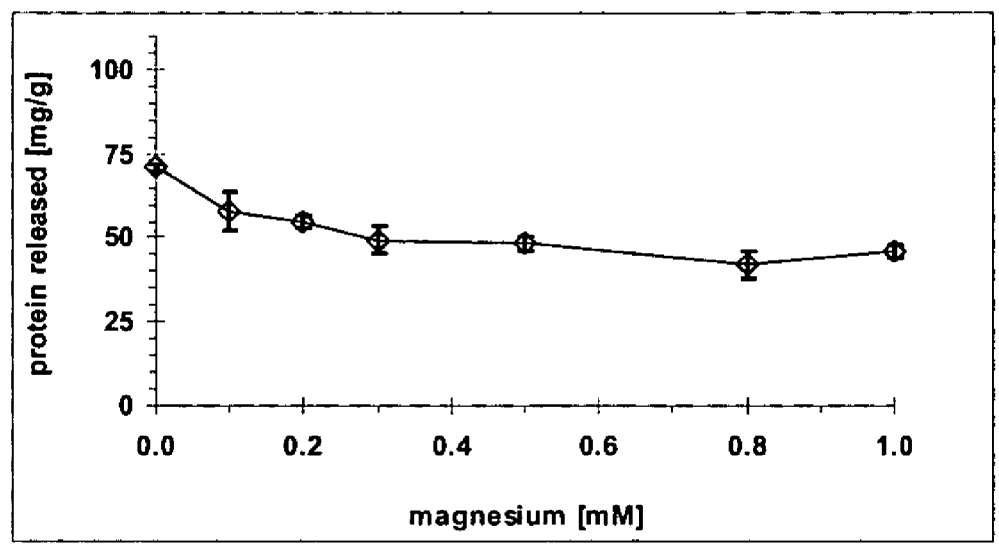

The presence of $Mg^{2+}$ is important to the native integrity of the bacterial cell wall. The $Mg^{2+}$ ion is incorporated into the cell wall and stabilizes the peptidoglycan. Calcium and other divalent metal ions will also function similarly. Thus the phenomenon that the presence of $Mg^{2+}$ are observed to reduce lysis, even when the λ R endolysin is expressed and the cells are put through a single freeze-thaw cycle. A lysis solution containing up to about 1 mM $Mg^{2+}$ shows about 75% lysis as measured by protein release. The lysis and protein release declines steadily as the $Mg^{2+}$ ion concentration increases, until a plateau is reaches at about 50%/50% lysis and protein release. Values are normalized to samples that were lysed by sonication, under conditions designed to give complete lysis (FIG. 10).

The use of *E. coli* strains and methods of the present invention including, but not limited to XJa, Xjb, and their DE3 lysogen progeny offer novel procedures to mediate bacterial lysis. The method is a highly efficient and regulatable system that utilizes arabinose induction of the λ R endolysin (or λ SR) coupled to a single freeze-thaw cycle. The methods are reproducible and faster than other protocols available to lyse bacteria. They are suitable for parallel processing of multiple samples as well as for scaling up to larger volumes.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described.

REFERENCES

Molecular Cloning A laboratory Manual, Third Edition, 2001, Joseph Sambrook and David W. Russell, Cold Spring Harbor Laboratory Press, Cold Spring Harbor N.Y.
Marvin and Witholt 1987, Amal. Biochem. 164: 320-330.
Ames et al. 1984, J. Bacteriol. 160: 1181-1183.
Cerny and Tueber 1971, Arch. Mikrobiol. 78: 166-179.
Goeddel et al 1979, P.N.A.S. 76: 106-110.
Schumacher et al. 1986, Nucleic Acid Res. 14: 5713-5727.
Chang C. Y. et al. J. Bacteriol. 1995, June; 177(11): 3283-3294.
Young et al. 1992 Microbiolgical Reviews, September. 430-481.
Datsenko and Wanner 2000, P.N.A.S., June 6, Vol. 97, 6640-6645.
Smith B. R. and Schleif. J. Biol. Chem. 1978 Oct. 10; 253 (19):6931-6933.
Botsford, J. L. et al. Microbiological Reviews 1992 March; (1): 100-122.
Cherepanov and Wackernagel 1995, Gene 158: 9-14.
Yanish-Perron et al. 1985; Gene 33: 103-119.
Studier et al. 1986, J. Mol. Biol. 189: 113-130. Studier et al. 1990, Methods in Enzymol. 185: 60-89:Davies and Jacob 1968, Cell 61: 956-978.
Bienkowska-Szewczyk et al. 1981, Mol. Gen. Genet. 184: 111-114.
Cox et al. 1983, P.N.A.S. USA 80:1141-1156.
Sternberg et al. 1994, J. Mol. Biol. 187: 197-212.
MacCaren and Clark 1996, Genomics 35: 299-307.
Deininger, 1983, Anal. Biochem. 135:247-263.
Hengen P. N., 1997, Trends Biochem. Sci. 22 325-330.
Koonin and Rudd 1994, Trends in Biochem. Sci. 19:106-107.
Holtjre, et al. 1975, J. Bacteriol. 124: 1067-1076.
Mett et al. 1980, J. Bacteriol 144: 45-52.
Fukagawa et al. 1993, 194: 733-740.
Engel et al. 1991, J. Bacteriol. 173: 6773-6782.
Thunnissen et al. 1994, Nature 367: 750-753.
Thunnissen et al. 1995, Biochemistry 34:12729-12737.

What is claimed is:

1. An E. coli strain comprising: the λR gene integrated in single copy into the E. coli genome at the arabinose operon as a cassette consisting of the λR gene and two FRT sites flanking a selectable marker, such that a portion of araB is replaced by the λR gene without disrupting the araA gene and the $P_{BAD}$ promoter, wherein the FTR sites provide short direct repeat target sequences for additional strain engineering or removal of the selectable marker by recombination between the FRT sites, and whereby the λR gene is inducible from the $P_{BAD}$ promoter at controlled levels that renders the E. coli strain susceptible to lysis after application of a brief physical-chemical stress and wherein the E. coli cell wall can be stabilized by addition of metal ions at about 1 mM.

2. The E. coli strain according to claim 1, wherein the strain is chosen from the group consisting of: XJa, XJb, XJa (DE3), and XJb (DE3), or the same strains that have the selectable marker gene removed via FLP recombinase.

3. The E. coli strain according to claim 1, wherein the E. coli strain lyses after application of a stress consisting of a single freeze thaw cycle.

4. The E. coli strain according to claim 1, wherein the E. coli strain lyses after application of a stress consisting of at least one freeze thaw cycle.

5. An E. coli strain comprising: the λSR genes integrated in single copy into the E. coli genome at the arabinose operon as a cassette consisting of the λSR genes and two FRT sites flanking a selectable marker, such that a portion of araB is replaced by the λSR genes without disrupting araA and the $P_{BAD}$ promoter, wherein the FTR sites provide short direct repeat target sequences for additional strain engineering or removal of the selectable marker by recombination between the FRT sites, and whereby the λR gene is inducible from the $P_{BAD}$ promoter at controlled levels that renders the E. coli strain susceptible to lysis after application of a brief physical-chemical stress and wherein the E. coli cell wall can be stabilized by addition of metal ions at about 1 mM.

6. The E. coli strain according to claim 5, wherein the E. coli strain lyses after application of a stress consisting of a single freeze thaw cycle.

7. The E. coli strain according to claim 6, wherein the E. coli strain lyses after application of a stress consisting of at least one freeze thaw cycle.

8. A method for controlled lysis of an *E. coli.* strain of claim 1 or 5 comprising:
  growing the *E. Coli* strain in media lacking arabinose to produce a starter culture;
  adding media containing arabinose and a metal ion at a concentration of higher than about 1 mM to the starter culture producing a diluted culture, wherein the arabinose induces expression of the λR or λSR genes and the higher than 1 mM metal ion concentration stabilizes the *E. coli*, cell wall,
  optionally growing the culture as needed for applications,
  harvesting the *E. coli*, from the arabinose and metal ion containing media to produce a cell pellet, re-suspending the cell pellet into a buffer containing a metal ion at a concentration of about 1 mM or less to produce a cell suspension,
  subjecting the suspension to a brief physical-chemical stress comprising,
  freezing the *E. coli* suspension,
  thawing the *E. coli* suspension, wherein the freeze-thaw causes the cells to lyse producing a cellular lysate, and;
  optionally repeating the freeze thaw-cycle.

9. The method of claim 8, wherein the metal ion is selected from the group consisting of magnesium and calcium.

10. The method of claim 5, further comprising treating the cellular lysate by a treatment selected from the group consisting of sonicating, vortexing, and nuclease.

11. The method of claim 5, further comprising centrifuging to remove cellular debris producing a cell free extract.

* * * * *